(12) United States Patent
Hoffman

(10) Patent No.: US 6,934,354 B2
(45) Date of Patent: Aug. 23, 2005

(54) COLLIMATOR ASSEMBLY HAVING MULTI-PIECE COMPONENTS

(75) Inventor: David M. Hoffman, New Berlin, WI (US)

(73) Assignee: General Electric Company, Milwaukee, WI (US)

( * ) Notice: Subject to any disclaimer, the term of this patent is extended or adjusted under 35 U.S.C. 154(b) by 129 days.

(21) Appl. No.: 10/249,714

(22) Filed: May 2, 2003

(65) Prior Publication Data

US 2004/0218713 A1 Nov. 4, 2004

(51) Int. Cl.[7] .............................................. A61B 6/00
(52) U.S. Cl. ........................................ 378/19; 378/149
(58) Field of Search ........................ 378/19, 147, 149, 378/186, 154; 250/370.09, 370.11

(56) References Cited

U.S. PATENT DOCUMENTS

| | | | | |
|---|---|---|---|---|
| 4,180,737 A | * | 12/1979 | Kingsley | 250/367 |
| 4,856,041 A | * | 8/1989 | Klein et al. | 378/147 |
| 5,033,074 A | * | 7/1991 | Cotter et al. | 378/147 |
| 6,091,795 A | * | 7/2000 | Schafer et al. | 378/19 |
| 6,553,092 B1 | * | 4/2003 | Mattson et al. | 378/19 |

* cited by examiner

Primary Examiner—Craig E. Church
Assistant Examiner—Jurie Yun
(74) Attorney, Agent, or Firm—Ziolkowski Patent Solutions Group, SC; Michael A. Della Penna; Carl B. Horton

(57) ABSTRACT

The present invention is directed to a collimator assembly defined by a series of multi-piece collimator elements or plates that extend along at least one dimension of a scintillator pack. Each collimator element has a collimating component and a shielding component that are structurally independent from one another. The collimating components may be connected to the shielding components or separated by a small air gap. The shielding components are wider than the collimating components but the collimating components have a greater height. With this construction, the collimator assembly optimizes collimation and shielding with lower material requirements and reduced overall size.

14 Claims, 6 Drawing Sheets

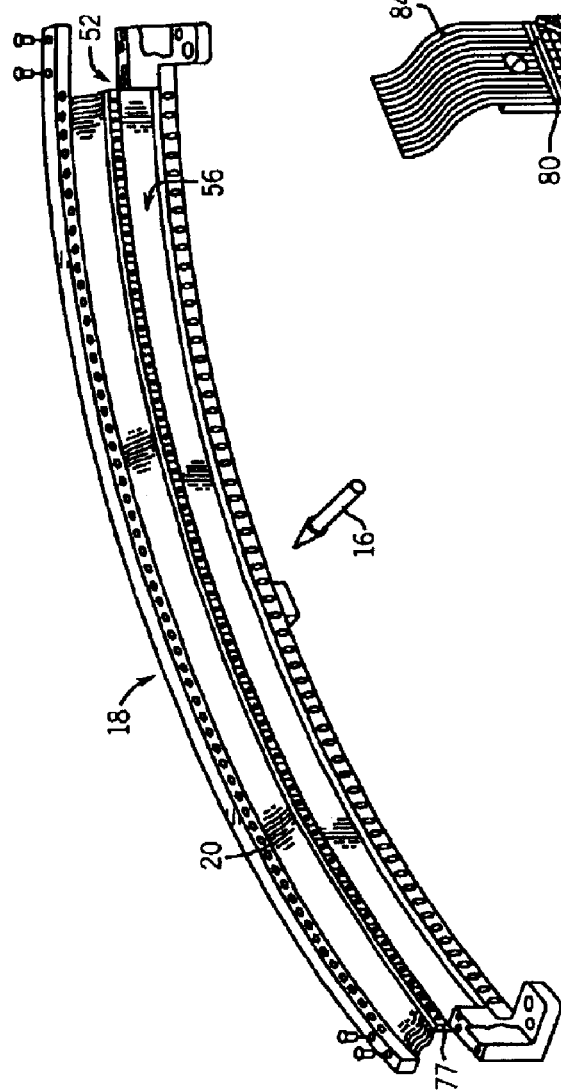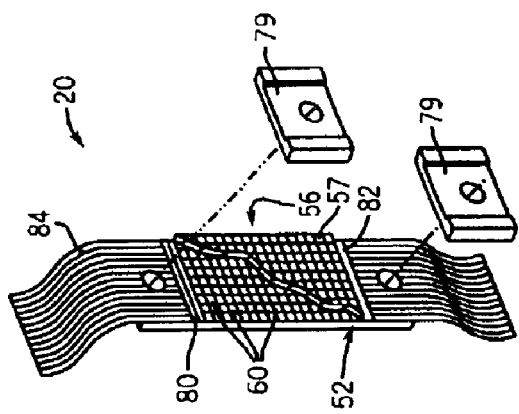
FIG. 3
FIG. 4

COLLIMATOR ASSEMBLY HAVING MULTI-PIECE COMPONENTS

BACKGROUND OF INVENTION

The present invention relates generally to diagnostic imaging and, more particularly, to a collimator assembly having collimating components independent of shielding components.

Typically, in computed tomography (CT) imaging systems, an x-ray source emits a fan-shaped beam toward a subject or object, such as a patient or a piece of luggage, along a projection path. Hereinafter, the terms "subject" and "object" shall include anything capable of being imaged, such as a medical patient. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated within the gantry about an imaging plane and around the subject. X-ray sources typically include x-ray tubes, which emit the x-ray beam at a focal point. X-ray detectors typically include a collimator for collimating x-ray beams received at the detector as well as reducing x-ray scatter, a scintillator for converting x-rays to light energy, a plurality of reflector elements disposed between the scintillators to reduce cross-talk emissions, and photodiodes for detecting the light output of the scintillators and producing electrical signals therefrom.

As stated above, typical x-ray detectors include a collimator assembly for collimating x-ray beams such that x-ray scattered by the patient and detected by the detector cells is minimized. Reducing this acceptance of scattered x-rays reduces image noise thereby improving the final reconstructed image. The collimator assembly is customarily a single structure defined by a plurality of plates or walls that extend along one or two dimensions above the scintillator array. Generally, the collimator plates have a width or thickness orthogonal to the projection path that is substantially similar to the width of the reflector material disposed between each of the scintillators. As such, it is paramount for the manufacturing and assembly processes to precisely align each of the plates of the collimator assembly with the reflector material gaps between scintillators thereby reducing scattering without blocking or minimizing the blocking of any of the active area or scintillator areas of the cells.

Known manufacturing processes attempt this exact alignment by constructing a continuous collimator assembly that is sized to dimensionally match the width and length of the entire detector array. That is, the scintillators are arranged in an array or pack and positioned on a tooling base such that the array or pack is fastened to the continuous collimator assembly. As such, the plates of the continuous collimator assembly must exactly align with the reflector walls or elements between each of the pixilated scintillator cells; otherwise, the collimator assembly must be discarded and a new collimator manufactured or the scintillator arrays or packs must be discarded and a new pack or array manufactured. This process requires excessively tight tolerancing and requires great operator skill and patience to assemble. Accordingly, these known processes are susceptible to waste of parts, material, and labor.

In addition to reducing x-ray scattering, known collimator assemblies also perform a shielding function. That is, the collimator assembly typically comprises relatively large amounts of tungsten that operate to reduce x-ray scattering. However, the amount of tungsten generally used exceeds that which is minimally required. The additional tungsten is used to increase the cross-sectional width of the collimator plates. The additional width is needed as a shield for various portions of the scintillator, reflector and photodiode. For example, it is not unusual for scintillator edges to be degraded during the manufacturing process. Further, it is common for exposed portions of reflector to discolor when exposed to x-rays or Î³-rays which negatively affect the reflectivity of the reflector. Furthermore, x-rays, without shielding, could penetrate the reflector and be absorbed by the photodiode array resulting in unwanted noise signals. Accordingly, the width of the collimator is generally increased with additional tungsten and other materials such that the degraded edges and otherwise-exposed reflector and the photodiode are "shielded" from direct x-ray impingement. Additionally, tungsten absorbs x-rays or Î³-rays and, as such, radiation dosage to the patient must be sufficient to accommodate the absorption characteristics of the tungsten. This standard construction is shown in FIG. 8.

Referring now to FIG. 8, a cross-sectional schematic diagram of a standard detector is shown. The detector 2 has a plurality of scintillators 3 arranged in an array 4 that are designed to output light upon the reception of high frequency electromagnetic energy such as x-rays or Î³-rays whereupon the light is detected by a photodiode array 5. The scintillators 3 are individually defined by a series of reflector elements or walls 6 that are connected by a reflector bridge or layer 7. The reflector elements 6 reduce cross-talk between adjacent scintillators 3. In front of or secured to the reflector layer 7 is a plurality of collimator plates or elements 8 that collectively form a collimator assembly 9. The collimator assembly 9 collimates radiation projected toward the scintillator array, reduces x-ray scatter and shields scintillator edges, otherwise-exposed reflector portions and shields the photodiodes from x-rays that penetrate the reflector layer 6. The width of each single piece collimator element 8 has a width $w_c$ that is substantially equal to or slightly wider than the width $w_r$ of each reflector element 6. As stated above, this rough or approximate equality of widths of the collimator elements and the reflector elements requires precise placement of the collimator assembly 9 to the scintillator array 4.

Additionally, as noted above, to sufficiently shield the scintillator edges, reflectors and photodiodes, the width of the collimator plates must be wider than is otherwise necessary for collimation and x-ray scatter reduction. Further compounding this size limitation is that a specified aspect ratio must be maintained. One skilled in the art will readily appreciate that "aspect ratio" is the dimensional ratio of the length or height of the collimator plates in the y-direction relative to the width between the collimator plates in the x-direction. As such, to maintain proper collimation, the height of each collimator plate must be made much larger than is needed to shield the scintillator edges, reflectors and photodiodes. All of which prolongs the manufacturing process, increases associated costs, and increases the amount of radiation necessary for data acquisition.

Therefore, it would be desirable to design a collimator assembly wherein collimating components are separated from shielding components. It would be further desirable to manufacture such a collimator assembly wherein the collimating components are thinner than the shielding components thereby improving manufacturing tolerances, reducing material needs, and reducing dosage requirements needed for ran imaging session.

BRIEF DESCRIPTION OF INVENTION

The present invention is directed to a collimator assembly having a number of multi-piece elements or components that overcomes the aforementioned drawbacks. The collimator assembly is defined by a series of collimator elements or plates that extend along at least one dimension. Each collimator element has a collimating component and a shielding component that are structurally independent from one another The collimating components may be connected to the shielding components or separated by a small air gap. Preferably the shielding components are wider than the collimating components but the collimating components have a greater height relative to the shielding components. With this construction, the collimator assembly optimizes collimation and shielding with reduced material requirements and reduced overall size.

Therefore, in accordance with one aspect of the present invention, a collimator for a CT detector array includes a first component and a second component. The first component is configured to collimate high frequency electromagnetic energy rays projected from a projection source toward a subject to be scanned along a projection path and whereas the second component is configured to shield at least one of a scintillator edge, a reflector, and a photodiode of a CT detector array.

In accordance with another aspect of the present invention, a CT system comprises a rotatable gantry having a bore centrally disposed therein and configured to receive a subject to be scanned and a table movable fore and aft through the bore and configured to position the subject for data acquisition. The CT system also includes a high frequency electromagnetic energy projection source positioned within the rotatable gantry and configured to emit high frequency electromagnetic energy toward the subject along a projection path. A CT detector array is provided and configured to receive high frequency electromagnetic energy impinged by the subject. The CT detector array includes a scintillator array configured to received high frequency electromagnetic energy and output light relative thereto. The detector array also includes plurality of collimating elements to filter high frequency electromagnetic energy scatter as well as a plurality of shielding elements secured to or in front of the scintillator array to at least shield scintillator edges from energy absorption. The CT detector array further includes a photodiode array configured to detect light output of the scintillator array and output a series of electrical signals. The CT system also has a DAS configured to receive the electrical signals from the photodiode array and an image reconstructor configured to reconstruct an image of the subject from the electrical signals received by the DAS.

According to another aspect of the invention, a method of manufacturing a CT detector array having individual detector cell optimization includes the steps of forming a scintillator pack defining a plurality of scintillators and depositing shielding elements on the scintillator pack between adjacent scintillators. The method also includes forming an array of collimator elements and aligning the array such that each collimator element generally aligns with a corresponding shielding element. A photodiode array is then coupled to the scintillator pack.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 3 is a perspective view of one embodiment of a CT system detector array.

FIG. 4 is a perspective view of one embodiment of a detector.

DETAILED DESCRIPTION

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
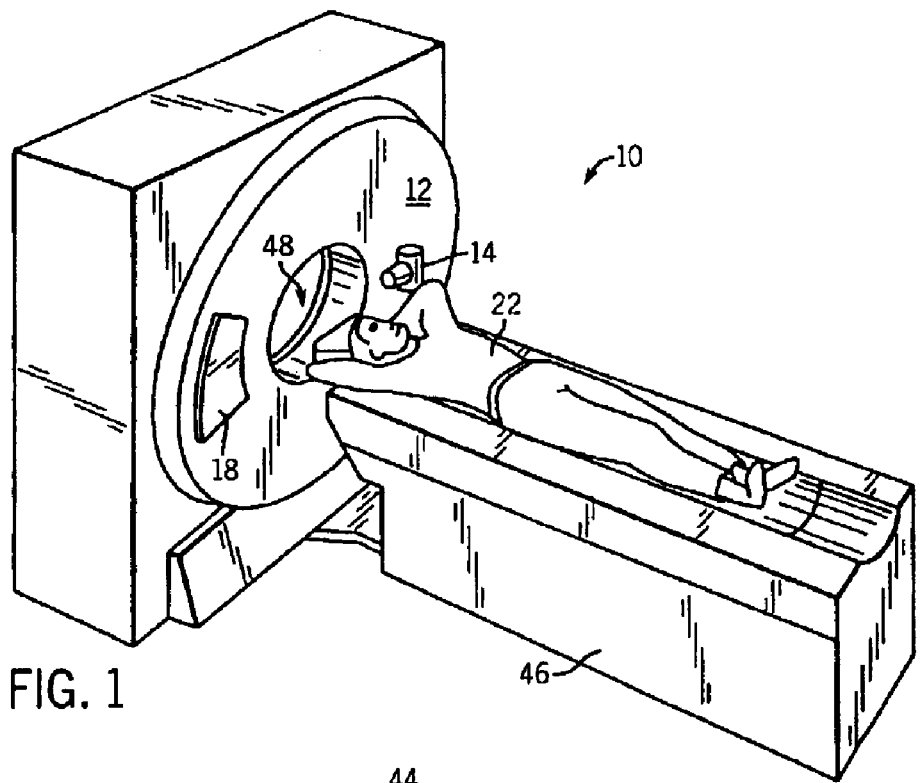
FIG. 1 is a pictorial view of a CT imaging system.
Figure 2:
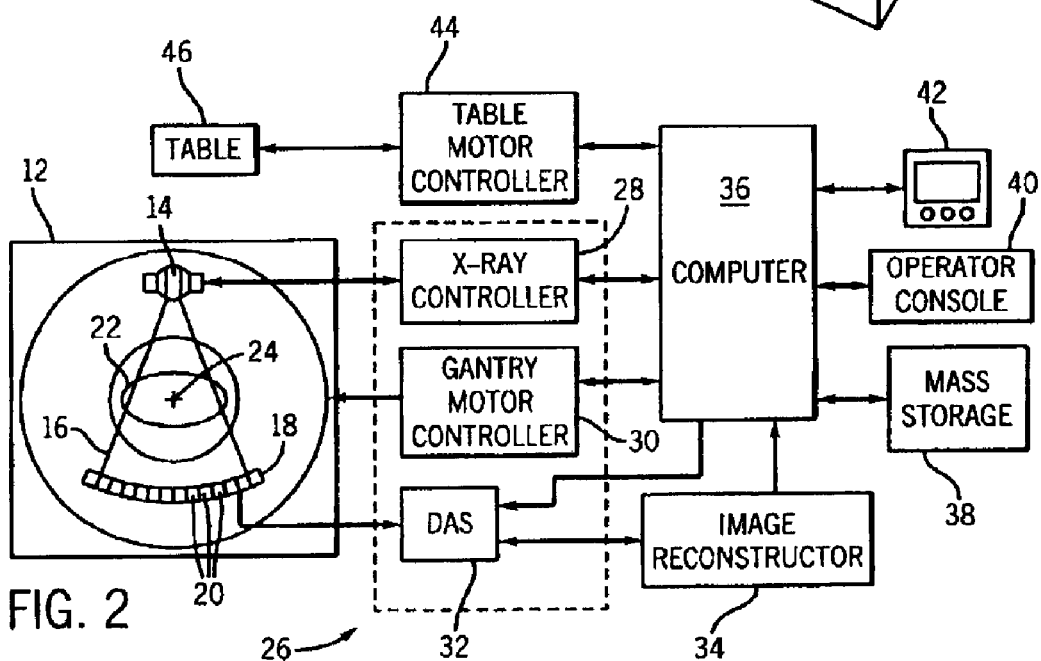
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of scintillators 57 forming a scintillator array 56. A collimator assembly (not shown) defined by a series of collimator plates or walls (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
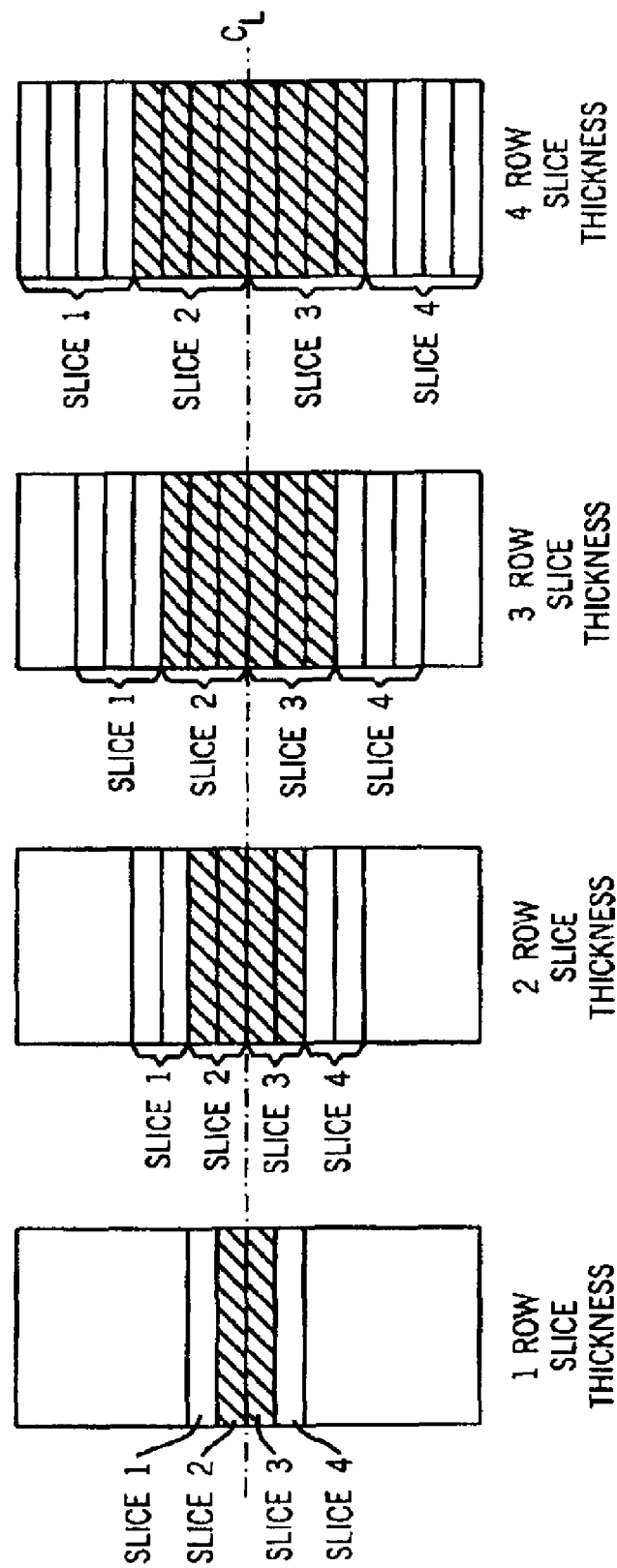
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
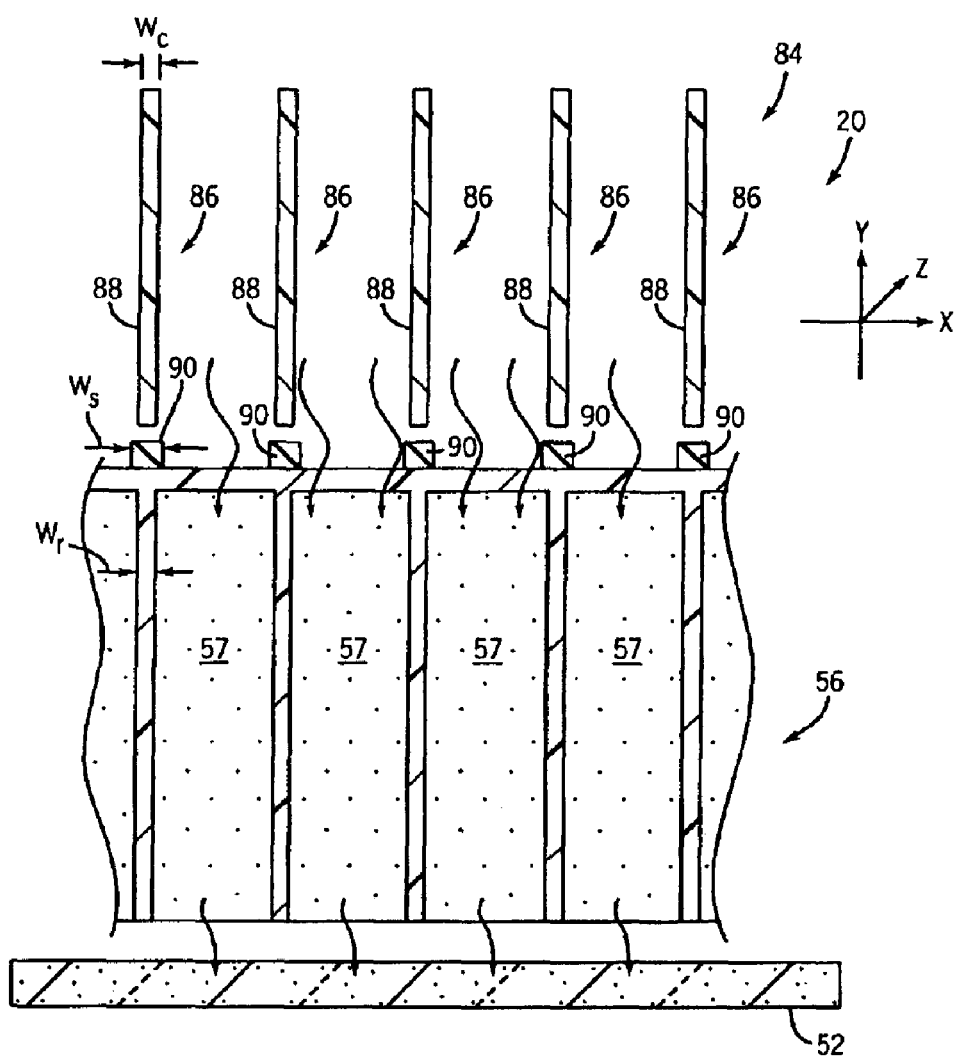
FIG. 6 is a cross-sectional schematic diagram of a detector in accordance with the present invention.

Referring now to FIG. 6, a CT detector having a collimator assembly with multi-piece components is schematically shown. The detector 20 includes a photodiode array 52 coupled to receive light emissions from a scintillator array 56 of scintillation elements 57. The scintillation elements 57 are constructed from a single or composite of materials designed to illuminate upon the reception of x-rays, $\hat{I}^3$-rays, or other forms of high frequency electromagnetic energy. The photodiode array 52 detects the light output of the scintillator array 56 and produces corresponding electrical signals that are processed and subsequently used to reconstruct an image of the subject.

Figure 8:
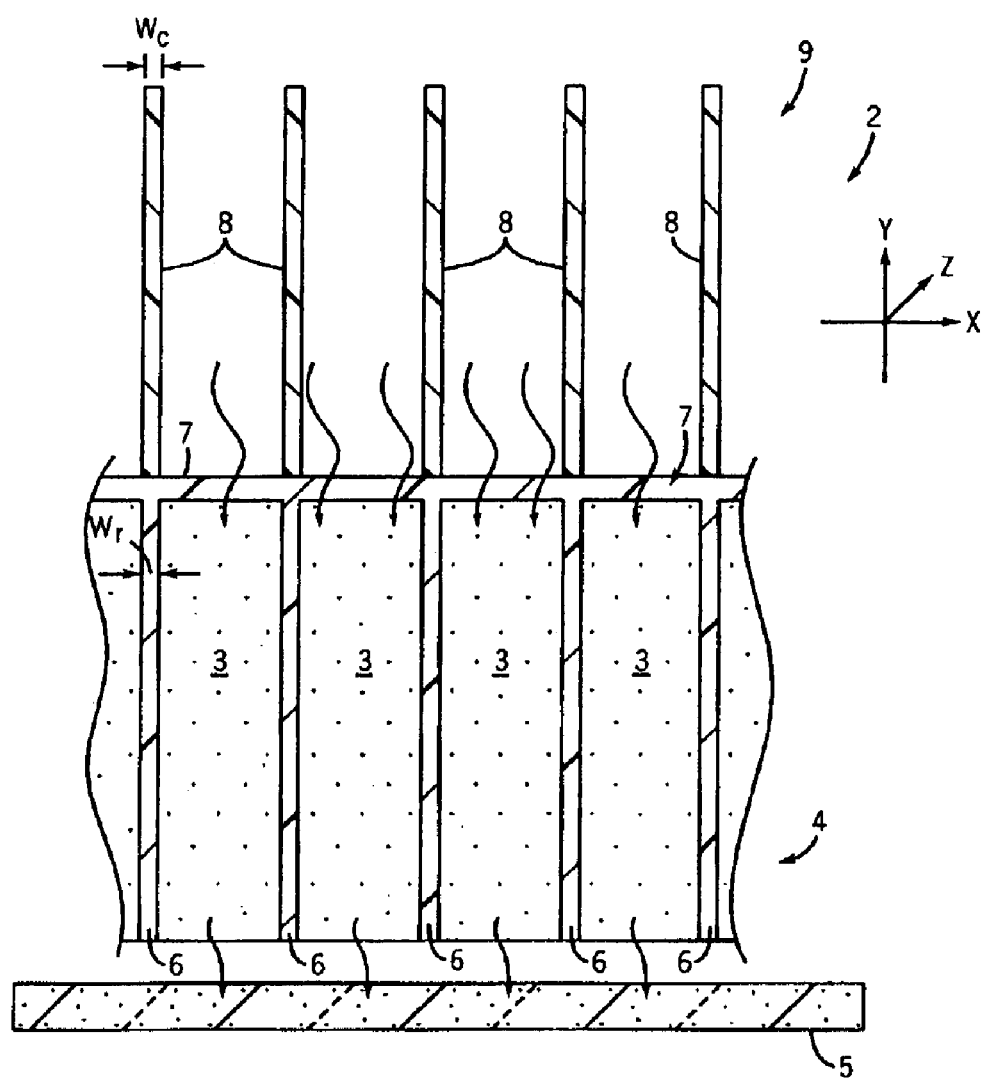
FIG. 8 is a cross-sectional schematic diagram of a known detector.

Similar to the known CT detector previously described with respect to FIG. 8, detector 20 includes a collimator assembly 84 to reduce x-ray scatter as well as shield scintillator edges, otherwise-exposed reflector, and the photodiodes of the photodiode array. However, unlike the detector of FIG. 8, the collimator assembly of CT detector 20 is defined by a plurality of multi-piece elements 86. In one embodiment, each element 86 has a single collimating component 88 and a single shielding component 90 that are structurally independent from one another and, as will be described below, dimensionally dissimilar from one another. That is, the width of each shielding component, $W_s$, is greater than the width of each collimating component, $W_r$.

Particularly, each collimating piece or component 88 is narrower in the x direction that the shielding components 90. Conversely, each collimating component 88 is dimensionally larger in the y-direction than the shielding components 90. The x-direction corresponds to the width of the CT detector whereas the y-direction corresponds to detector height. As such, the proper aspect ratio for collimation is maintained but an optimal amount of collimating material may be used since the collimating components 88 are not operating as shielding components. In contrast, as the shielding components 90 are not responsible for collimation, a specified aspect ratio of the shielding components is not required. Accordingly, the shielding components 90 must only have a sufficient width to achieve shielding of the degraded scintillator edges and otherwise-exposed reflector material. As such, the shielding components 90 may have a width of approximately 200 microns but the collimating components 88 may have a width as narrow as 25 microns or less.

The narrowing of the collimating elements relative to the shielding elements has a number of advantages. For example, first, the differences in width allow for more tolerancing in the placement of the collimator assembly. That is, because the collimating elements are narrower than the shielding elements there is more latitude in placement of the collimator assembly as well as spacing of the collimator elements relative to one another. Second, the reduced width of the collimator elements reduces the material costs of the collimator assembly. Third, narrowing of the collimator elements increases the number of x-rays or $\hat{I}^3$-rays received by each scintillator. As a result, radiation detection or QDE (Quantum Detection Efficiency) is improved. Fourth, x-ray blockage is reduced thereby improving low signal performance of the CT detector. Fifth, a byproduct of improved low signal performance is that radiation dosage to the subject may also be reduced. One skilled in the art will readily appreciate that numerous other advantages separate from those explicitly enumerated may be achieved in accordance with the above described configuration.

The multi-piece collimator elements of the aforedescribed collimator assembly are structurally independent of one another. As such, the collimating elements may be fabricated from materials dissimilar from the materials used to form the shielding elements. Preferably, however, materials having high atomic numbers should be used for both the collimating elements and the shielding elements. For example, loaded epoxies, lead, lead alloys, and the like may be used to form the shielding elements. Additionally, the collimating elements and the shielding elements may be formed of composite or cast materials and fabricated in accordance with a number of known techniques. In one exemplary technique, the shielding elements are formed using well-known semiconductor fabrication processes whereupon a layer of shielding material is etched, i.e. chemically etched, to create a series of shielding elements. Because the shielding elements are relatively short in the y-direction, chemically etching is one preferred fabrication process.

Other fabrication processes may be implemented including laser cutting, ion beam milling, or securing a shielding element grid to the scintillator array with a thin adhesive layer. The shielding elements may also be formed during a casting process whereupon a mold defining a desired height and width for a plurality of shielding elements is placed atop the scintillator pack and filled with shielding material that upon curing and post-processing (i.e. grinding) a plurality of shielding elements integrated with the scintillator pack is formed. Further, the mold may be constructed to define a series of collimating cavities that are deeper and narrower than a series of shielding cavities such that the shielding cavities are first filled with shielding material(s) and allowed to cure. Thereafter, the collimating cavities are filled with collimating material(s). With this construction, the shielding elements are independent and dimensionally dissimilar from the collimating elements but are connected to one another thereby minimizing the gap between the elements shown in FIG. 6.

The present invention has been described with respect to fabrication of integrated scintillator and collimator for a CT detector of a CT imaging system. CT detectors incorporating a collimator assembly having collimating elements independent of shielding elements in accordance with the present invention may be used in medical imaging systems as well as parcel inspections systems similar to those illustrated in FIG. 7.

Figure 7:
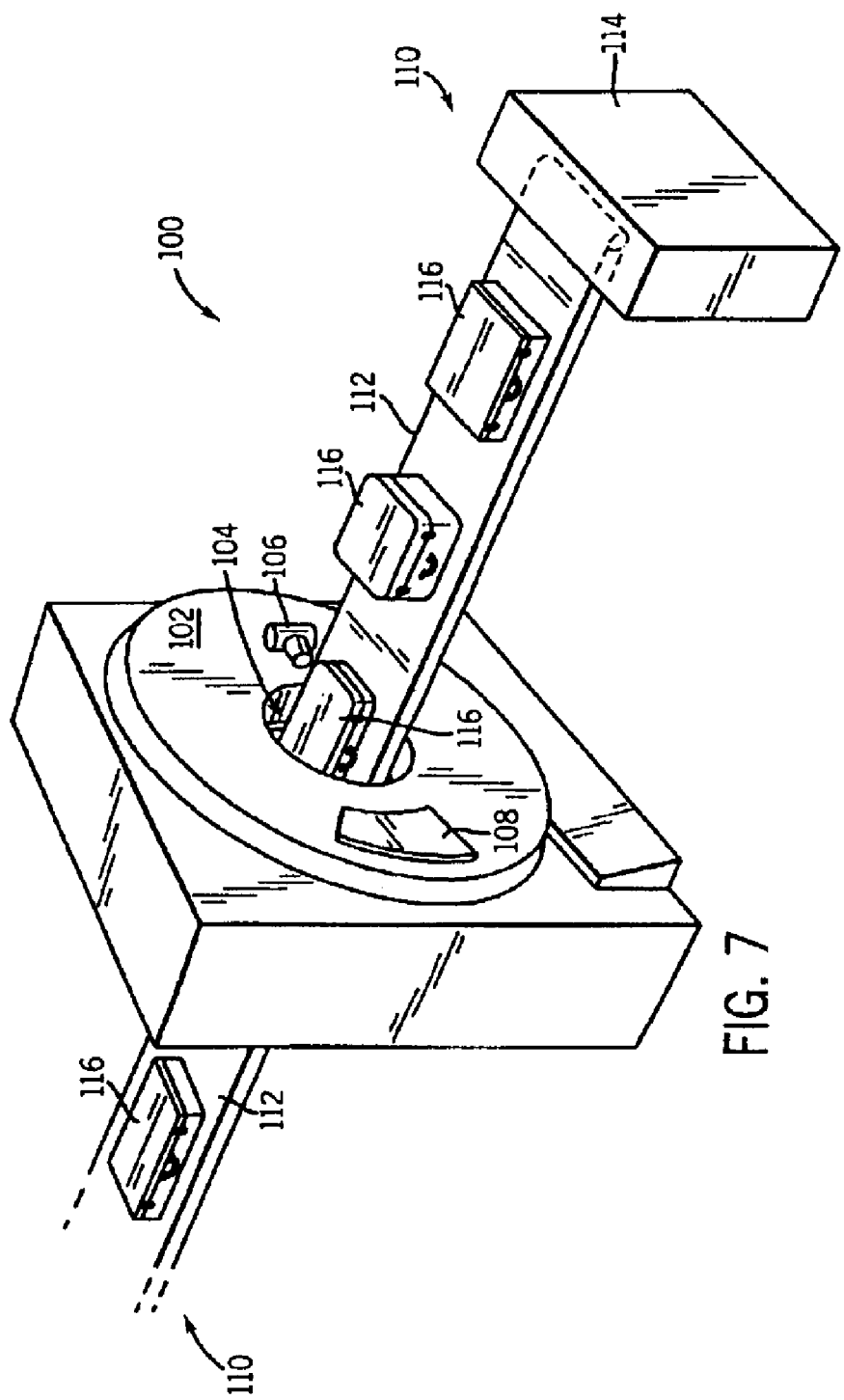
FIG. 7 is a pictorial view of a CT system for use with a non-invasive package inspection system.

Referring to FIG. 7, package/baggage inspection system 100 includes a rotatable gantry 102 having an opening 104 therein through which packages or pieces of baggage may pass. The rotatable gantry 102 houses a high frequency electromagnetic energy source 156 as well as a detector assembly 108 having CT detectors similar to that previously described. A conveyor system 110 is also provided and includes a conveyor belt 112 supported by structure 114 to automatically and continuously pass packages or baggage pieces 116 through opening 114 to be scanned. Objects 166 are fed through opening 104 by conveyor belt 112, imaging data is then acquired, and the conveyor belt 112 removes the packages 116 from opening 114 in a controlled and continuous manner. As a result, postal inspectors, baggage handlers, and other security personnel may non-invasively inspect the contents of packages 116 for explosives, knives, guns, contraband, etc.

Additionally, the present invention has been described whereupon the collimator plates are cast along one dimensional, i.e. the x-axis. However, the collimator plates may be formed along an x and z axis thereby rendering a "checkerboard" arrangement of multi-piece collimator elements.

Therefore, in accordance with one embodiment of the present invention, a collimator for a CT detector array includes a first component and a second component. The first component is configured to collimate high frequency electromagnetic energy rays projected from a projection source toward a subject to be scanned along a projection path and whereas the second component is configured to shield at least one of a scintillator edge, a reflector, and a photodiode of a CT detector array.

In accordance with another embodiment of the present invention, a CT system comprises a rotatable gantry having a bore centrally disposed therein and configured to receive a subject to be scanned and a table movable fore and aft through the bore and configured to position the subject for data acquisition. The CT system also includes a high frequency electromagnetic energy projection source positioned within the rotatable gantry and configured to emit high frequency electromagnetic energy toward the subject along a projection path. A CT detector array is provided and configured to receive high frequency electromagnetic energy impinged by the subject. The CT detector array includes a scintillator array configured to received high frequency electromagnetic energy and output light relative thereto. The detector array also includes plurality of collimating elements to filter high frequency electromagnetic energy scatter as well as a plurality of shielding elements secured to the scintillator array to at least shield scintillator edges from energy absorption. The CT detector array further includes a photodiode array configured to detect light output of the scintillator array and output a series of electrical signals. The CT system also has a DAS configured to receive the electrical signals from the photodiode array and an image reconstructor configured to reconstruct an image of the subject from the electrical signals received by the DAS.

According to another embodiment of the invention, a method of manufacturing a CT detector array having individual detector cell optimization includes the steps of forming a scintillator pack defining a plurality of scintillators and depositing shielding elements on the scintillator pack between adjacent scintillators. The method also includes forming an array of collimator elements and aligning the array such that each collimator element generally aligns with a corresponding shielding element. A photodiode array is then coupled to the scintillator pack.

The present invention has been described in terms of the preferred embodiment, and it is recognized that equivalents, alternatives, and modifications, aside from those expressly stated, are possible and within the scope of the appending claims.

What is claimed is:

1. A CT system comprising:
    a rotatable gantry having a bore centrally disposed therein and configured to receive a subject to be scanned;
    a table movable fore and aft through the bore and configured to position the subject for data acquisition;
    a high frequency electromagnetic energy projection source positioned within the rotatable gantry and configured to emit high frequency electromagnetic energy toward the subject along a projection path;
    a CT detector array configured to receive high frequency electromagnetic energy impinged by the subject, the CT detector array including:
        a scintillator array configured to received high frequency electromagnetic energy and output light relative thereto;
        a plurality of collimating elements to filter high frequency electromagnetic energy scatter;
        a plurality of shielding elements secured to the scintillator array to at least shield scintillator edges from energy absorption; and a photodiode array configured to detect light output of the scintillator array and output a series of electrical signals;

a DAS configured to received the electrical signals from the photodiode array; and an image reconstructor configured to reconstruct an image of the subject from the electrical signals received by the DAS.

2. The CT system of claim 1 wherein each shielding element has a width greater than a width of each collimating element along an x-axis.

3. The CT system of claim 2 wherein each collimating element has a width not exceeding approximately 200 microns.

4. The CT system of claim 3 wherein each collimating element has a width not exceeding approximately 50 microns.

5. The CT system of claim 4 wherein each collimating element has a width of approximately 25 microns.

6. The CT system of claim 1 where the plurality of collimating elements and the plurality of shielding elements are fabricated from at least one material having a high atomic number.

7. The CT system of claim 1 wherein the plurality of shielding elements is fabricated from one of composite materials and cast materials.

8. The CT system of claim 1 incorporated into a medical imaging scanner.

9. A method of manufacturing a CT detector array having individual detector cell optimization, the method comprising the steps of:

forming a scintillator pack defining a plurality of scintillators;

depositing shielding elements on the scintillator pack between adjacent scintillators;

forming an array of collimator elements and aligning the array such that each collimator element generally aligns with a corresponding shielding element; and coupling a photodiode array to the scintillator pack.

10. The method of claim 9 wherein the shielding elements are independent of the collimating elements.

11. The method of claim 9 wherein the step of depositing the shielding elements includes the step of directly casting shielding material between adjacent scintillators.

12. The method of claim 11 wherein the step of depositing further includes the step of etching a layer of shielding material applied to tho scintillator pack.

13. The method of claim 9 wherein each collimator element has a thickness that exceeds a thickness of each shielding element along a y-axis.

14. The method of claim 13 wherein each collimating element has a width not exceeding approximately 50 microns.

* * * * *